United States Patent [19]

Yang

[11] 4,375,163

[45] Mar. 1, 1983

[54] METHOD AND APPARATUS FOR ON-COLUMN DETECTION IN LIQUID CHROMATOGRAPHY

[75] Inventor: Frank J. Yang, Danville, Calif.

[73] Assignee: Varian Associates, Inc., Palo Alto, Calif.

[21] Appl. No.: 223,445

[22] Filed: Jan. 8, 1981

[51] Int. Cl.³ .............................................. G01N 31/08
[52] U.S. Cl. .............................. 73/61.1 C; 210/198.2; 250/373
[58] Field of Search ..................... 73/61.1 C; 250/373, 250/372; 356/410, 411; 210/198.2, 656

[56] References Cited

U.S. PATENT DOCUMENTS 3,518,009  6/1970  Shamos et al. .................. 356/410 X
4,207,188  6/1980  Tsuda et al. ..................... 210/198.2

Primary Examiner—Edward R. Kazenske
Assistant Examiner—Joseph W. Roskos
Attorney, Agent, or Firm—Stanley Z. Cole; Norman E. Reitz

[57] ABSTRACT

On-column detection by an optical detector is accomplished with a flexible silica column. The flexible fused silica column has an inner diameter less than 500 μm, an external protective coating with a stripped portion near the end of the column. The stripped portion is placed in the working path of an optical detector in order to detect and resolve the sample.

10 Claims, 10 Drawing Figures

METHOD AND APPARATUS FOR ON-COLUMN DETECTION IN LIQUID CHROMATOGRAPHY

DESCRIPTION

This invention relates to sample detection in the field of chromatography and, more particularly, relates to a method and apparatus for on-column detection in high resolution liquid chromatography.

In the field of chromatography, separation of species is accomplished by flowing a sample containing multiple species in a carrier gas or liquid through a column containing a stationary phase. The species within the sample are separated on the basis of their relative transit time through the column. The species are detected at different time intervals by means such as ionization detectors, spectrophotometric detectors, spectrofluorometric detectors, electrochemical detectors and the like. Since these detectors are attached to the end of chromatographic columns an interconnection between the column and the detector is required. These interconnections invariably introduce mixing effects and dead volume which result in the loss of resolution between peaks especially if the peaks are close together and especially when the cross-section of the interconnection tube becomes much larger than the cross-section of the column. This problem has become exacerbated as the field of chromatography has progressed to the use of microcolumns having inner-diameters of 500 microns or less. In such cases, it has become increasingly difficult, if not impossible, to provide interconnections which do not introduce substantial mixing effects, since, even though the absolute volumes are small, the cross-sectional areas of the column, interconnection and flow cell may be much different. In addition, it has been difficult to fabricate and attach detectors with volumes as small as those found within the columns themselves.

Microcapillary liquid chromatography has rapidly progressed to the use of columns having inner diameters in the range of 30–60 microns. See e.g., D. Ishii, et al. "Study of Open-Tubular-Micro-Capillary Liquid Chromatography", *J. High Resolution Chromatography & Chromatography Communications*, June 1979, p. 371. The use of such columns leads to severe discontinuities between the column and the detector. This discontinuity in inner diameters may be of the following type: a column having inner diameter of 30–60 microns may be succeeded by connectors having inner diameters of 130 microns and 70 microns, respectively, and a detector having an inner diameter of 170 microns (D. Ishii, supra, p. 373); and a capillary column having an inner diameter of 60 microns followed by an interconnection having an inner diameter of 150 microns and a detector having an inner diameter of 300 microns (P. Tsuda, "Studies of Open Tubular Micro-Capillary Liquid Chromatography", J. Chromatogr., V. 158, P. 227, 229 (1978)). It is evident that even though the inner diameters involved are small, there are great differences among the successive links so that at the interface severe mixing effects and dead volume effects will be experienced. Such effects necessarily reduce the resolution between peaks.

Fused silica columns are now being used in place of capillary columns in gas chromatography and in liquid chromatography. See F. J. Yang, "Fused Silica Open Tubular Column for Liquid Chromatography", J. High Resolution Chromatography and Chromatography Communications, p. 589, November, 1980, and references cited therein. The advantage of fused silica columns is that they can be drawn on heating to exceedingly small diameters and active absorbents can be internally bonded for use in producing chromatographic separation. In addition, fused silica columns have excellent mechanical strength and optical properties and when drawn down to sufficiently small diameters, as described subsequently, are flexible. For a discussion of the utility of narrow diameter glass columns, see T. Tsuda, et al. U.S. Pat. No. 4,207,188, "Open Tubular Capillary Column for High-Speed Micro-Liquid Chromatography".

On-column flourescence detection has previously been accomplished. In B. F. Lloyd, "Nitrogen Heteracycle and Polynuclear Hydrocarbon Flourescence and Adsorption Effects in the Presence of Silica Gel-Applications in High-Pressure Liquid and Microcolumn Chromatography", *The Analyst*, v. 100, pp. 529, 531 (1975), a 3.5 mm outer diameter, 1 mm inner diameter microcolumn is constricted at one end by heating to have an inner diameter of approximately 0.1 mm. The cell, i.e., the constricted region, was packed with a dry absorbent which was retained between cotton or glass fibre plugs. As sample was flowed through the constricted region at flow rates of up to 2 ml per minute the flourescence emanating from the absorbent was monitored by a microscope. In this instance of on-column detection, the column was rigid since it was 1000 μm in inner diameter and was not transparent due to the inclusion of packing material.

SUMMARY OF THE INVENTION

On-column detection is accomplished by optical means with a flexible fused silica column. The flexible column is internally activated, has an inner diameter less than 500 μm, and an external protective coating with a portion thereof stripped near the end of the column. The stripped portion is placed in the working path of an optical detector while a sample is flowed through the column in order to detect and resolve the sample.

BRIEF DESCRIPTION OF THE DRAWINGS

For a more complete understanding of the method and apparatus of the present invention, reference may be made to the accompanying drawings which are incorporated herein by reference and in which.

DESCRIPTION OF THE PREFERRED EMBODIMENTS

Figure 1A:
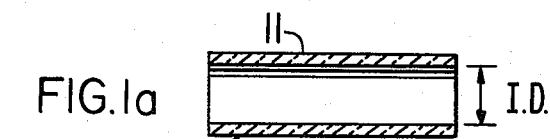
FIGS. 1a–1f illustrate the steps for fabricating a microcapillary column suitable for on-column detection in accordance with the present invention.
Figure 1B:
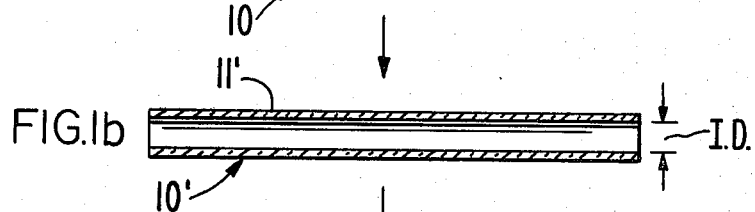
Figure 1C:
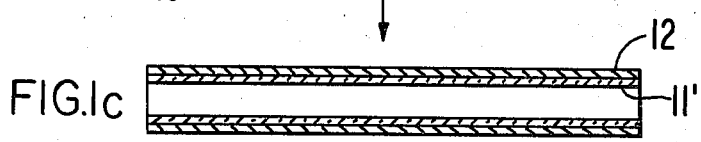

The conventional wisdom has been that it is not feasible to detect the separation of constituents within a sample while it is yet flowing at the end of a chromatographic column. This was not believed to be feasible especially for visible optical detection because conventional column materials have not had acceptable optical properties. An exception is the flourescence detection of the Lloyd article discussed above. For visible optical detection, however, soda lime and borosilicate glass have had unacceptably high optical absorption and metal columns have been opaque. In addition, ordinary glass columns have not been able to operate at pressures up to 750 atmospheres which are required for high resolution liquid chromatography. The method of the present invention, however, utilizes fused silica both for a continuous chromatographic column and for an integral detector flow cell. Fused silica is much stronger than other glasses due to the internal bonding. As a consequence, it requires temperatures of 1800°–2000° C. to be drawn as compared with 400° C. for soda lime glass and 700° C. for pyrex. Fused silica columns which are drawn down to have inner diameters to less than 500 μm are flexible and may be coiled with large lengths fitting in small volumes. This fused silica is now commercially available for use in gas chromatography columns with inner diameters of less than 300 microns. See, e.g., R. Dandeneau, et al., "Flexible Fused Silica Columns", *American Laboratory*, June 1979; Alltech Associates, Product Bulletin No. 37, p. 1 (1980). The use of the end of a fused silica column itself as a flow cell for detection in the present invention enhances sensitivity and preserves chromatographic resolution because concentration is high and sharp peaks are seen.

Some ingenious approaches to low dead volume detectors which have been developed and reported are (1) laser fluorimetry, G. J. Diebold and R. N. Zare, "Laser Fluorimetry: Subpicogram Detection of Alfatoxins Using High-Pressure Liquid Chromatography", *Science* 196, 1439–1441 (1977); (2) miniaturized UV detectors, D. Ishii, et al. "A Study of Micro-High-Performance Liquid Chromatography to Development of Technique for Miniaturization of High-Performance Liquid Chromatography", *J. Chromatogr.* 144, 157–168 (1977); (3) Y. Hirata, et al., "Packed Microcapillary Columns With Different Selectivities for Liquid Chromatography", *Anal. Chem.* 51, 1807–1809 (1979); (4) miniaturized electro-chemical detectors, Y. Hirata, et al., "Small-Volume Electrochemical Detector for Microcolumn Liquid Chromatography", *J. Chromatogr.* 181, 287–294 (1980); (5) a sheath flow fluorometric detector, L. W. Hershberger, et al., "Sub-Microliter Flow-Through Cuvette for Fluorescence Monitoring of High Performance Liquid Chromatographic Effluents", *Anal. Chem.* 51, 1444–1446 (1979); and (6) the free falling drop fluorometric detector, F. Martin, et al., "The Free-Falling Drop Detector—A Novel Fluorescence Detector for High Performance Liquid Chromatography", *Clin. Chem.* 22, 1434–1437 (1979). Among these, the UV and spectro-fluorometric detectors are the most trouble-free and most frequently used. The availability of low dead volume UV and spectrofluorometric detectors are an important factor in permitting small-bore column LC to become a powerful separation technique for routine applications. Yet, a limitation to these low dead volume detectors is that the flow cell volumes between 0.1 and 0.3 μL are far from the optimum desirable for small-bore column LC. For example, in small-bore column liquid chromatography, it has been theoretically derived that detector flow cell volumes of 1–10 nl are required for achieving less than 1% loss of peak resolution on a 10 to 50 μm diameter open tubular column, for a retained peak with partition ratio $k=10$ and retention time=1 hour. See J. Knox, et al. "Kinetic Optimazation of Straight Open-Tubular Liquid Chromatography", *J. Chromatogr.*, v. 186, pp 405–418 (1979). In addition, the extra band broadening caused by column to detector connections and interface tubing significantly affect performance. The method and apparatus of the present invention serves to eliminate effects due to column-to-detector interconnection and detector dead volume effects due to mixing.

METHOD

The method of the present invention is illustrated in the Figures and particularly in FIGS. 1a–1f. A fused silica column 10, shown in cross-section in FIG. 1a, is selected with a wall thickness 11 on the order of 24 mm and an inner diameter ID less than 20 mm. The fused silica column 10 is then drawn under thermal treatment in a fiber optics drawing machine at temperatures on the order of 2000° C. The drawing rate (ratio of extraction rate/insertion rate) can be varied from greater than one up to 1000. As this rate is increased both the inner diameter and the wall thickness decreases. The reduced inner diameter will typically be less than 500 μm and the reduced wall thickness 11' will be between 20 and 150 μm. Such columns are of the type which are commercially available for gas chromatography as described above. Larger diameter columns are typically not flexible and are therefore not encompassed within the method of the present invention. The drawn column 10' is flexible but fragile. For protection a polymer coating 12 such as polyimide or a metallic coating is applied externally; typically the external coating has a thickness between 10 and 150 μm.

Figure 1D:
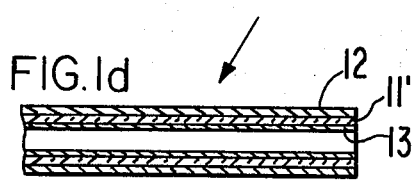
Figure 1E:
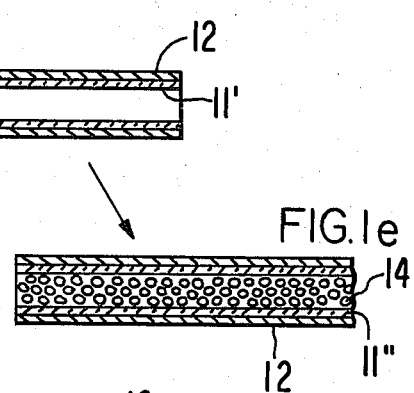
Figure 1F:
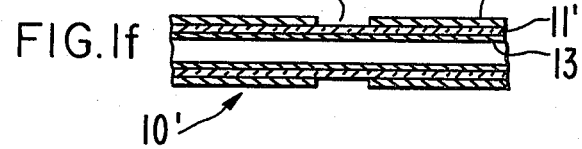
Figure 2:
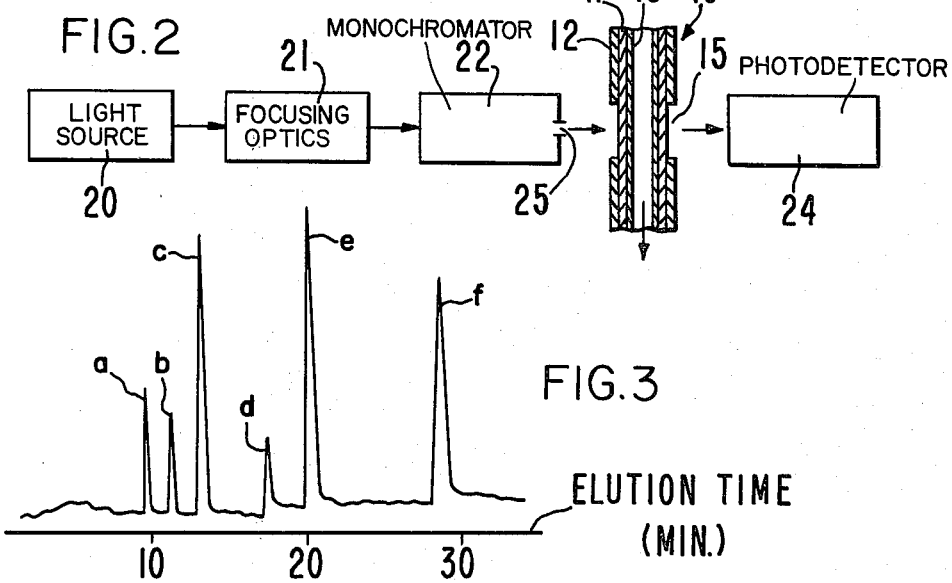
FIG. 2 depicts an on-column ultraviolet detection apparatus used in conjunction with the apparatus of the present invention.

As shown in FIGS. 1d and 1e, the fused silica column is activated either by coating the interior with a stationary phase 13 or by chemically bonding a stationary phase 13 to the interior surface of the column or by packing the columns with activated microparticles 14. At the lowest inner column diameters (those approaching the diameters of the microparticles), coatings may be more practible than packings, although packing techniques such as disclosed in K. Mochizuki, et al., "Column for use in High Speed Liquid Chromatography", U.S. Pat. No. 4,059,523 may be used. The art of coating or packing is well established and most conventional approaches may be used. See L. R. Snyder, et al., *Introduction to Modern Liquid Chromatography*, 9.2, "Column Packings" p. 287 et seq. Next, as shown in FIG. 1f, the external protective coating is removed along a short segment of the coated or packed fused silica microcapillary column. Removal is accomplished by scraping, dissolving or thermally decomposing the coating. This segment is of the order of 1 cm or less and is sufficient to permit access by a visible light optical detector through the column. In effect, a flow cell is produced without having to interconnect separate pieces. The volume of this cell may be as small as 0.24 μL when the inner diameter of the column is 10 μm. The exposed segment of the fused silica column 15' is then placed in the optical path of an ultraviolet photodetector, such as a Jasco UVIDEC III or a Varichrome UV-50, as shown in FIG. 2. In an alternative embodiment the activating layer 13 is also removed along the end of the fused silica column up to and including the short segment to eliminate any absorption of visible light by the thin film. Removal is accomplished by external application of heat or by dipping the end of the column in a suitable solvent. For packed columns the activated microparticles 14 are kept from the flow cell by a frit positioned upstream.

STRUCTURE

Figure 3:
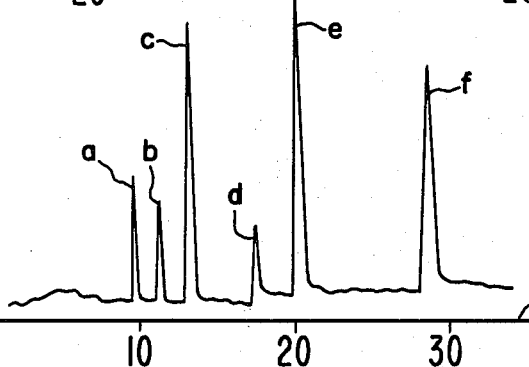
FIG. 3 is a chromatogram of components of a sample which were separated by the apparatus of the present invention.

The apparatus for accomplishing on-column detection in accordance with the present invention is shown in FIGS. 2 and 3. In FIG. 2 a UV detector such as a Jasco UVIDEC III is utilized. The UV detector comprises a light source 20, focusing optics 21, monochromator 22 having an exit slit 25 and a photodetector 24. In lieu of a flow cell, a passageway is provided for the fused silica column 10'. The exposed segment 15 is placed across the optical path so that photodetector 24 receives light that has passed through a full diameter of the column which has a sample flowing through it. The flow rate is not a limiting factor and may be as great as 10 ml/min. In an alternative embodiment a multiple wavelength UV detector such as Varian Varichrome UV-50 may be employed. The system arrangement is the same with the wavelengths being selected to permit several substances to be detected simultaneously.

Since there is negligible mixing in the on-column detector of the present invention, the extra-column band broadening contribution to the percent loss of resolution, %ΔR, can be expressed by $$\% \Delta R = \frac{R_c - R}{R_c} \cdot 100\% = \left( 1 - \left[ 1 + \frac{hl}{HL} \right]^{-\frac{1}{2}} \right) \cdot 100\% \quad (1)$$

where
$R_c, R$ = resolution measured for the column and the combination of column and detector, respectively
$h, H$ = the height equivalent to a theoretical plate for the flow cell and the column, respectively
$l, L$ = the entrance/exit slit length for the flow cell and the column length, respectively.

For a circular cross-sectional column, as an example, h, and H can be expressed by equations (2) and (3), respectively.

$$h = \frac{2D_m}{U} + \frac{r^2 U}{24 D_m} \quad (2)$$

$$H = \frac{2D_m}{U} + \frac{(1 + 6k' + 11k'^2)}{24(1 + k')^2} \cdot \frac{r^2 U}{D_m} + \frac{2k' d_f^2 U}{3(1 + k')^2 D_l} \quad (3)$$

where
r = column radius
U = the average linear flow velocity for the mobile phase
$D_m$ & $D_l$ = are the diffusivities for the solute molecules in the mobile and the stationary phases, respectively
$d_f$ = the stationary phase film thickness
k' = the partition ratio for the solute molecules = true retention time/column void time.

Figure 4:
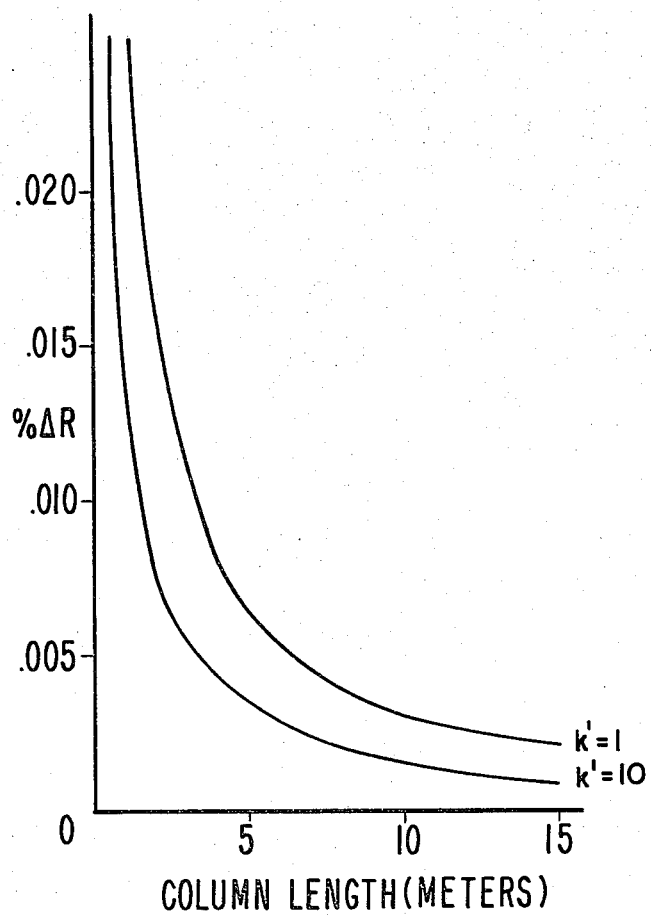
FIG. 4 is a graph illustrating the contribution to the loss of resolution produced by the on-column detector of the present invention for two retained components with partition constants of 1 and 10, respectively.

Using these equations, the contribution of the on-column detector of the present invention to % R for two retained components with partition ratios, k', of 1 and 10 on a column with length up to 15 meters is given in FIG. 4. Flow rate and $D_m$ are assumed to be 1 μL/min and 1×10$^{-5}$ cm²/sec, respectively. The length of the detector is 0.3 cm. Column diameter is assumed to be 150 μm. For conventional optical detectors the associated flow cells may make a significant contribution, on the order of tens of percent, to loss of resolution. As shown in FIG. 4, even for a partition ratio approaching 1, (a lower limit for a chromatographic column performing good separation) there is a contribution by the on-column detection "cell" to loss of resolution of the order of hundredths of a percent. As expected, the higher the partition ratio, the less the contribution to loss of percent resolution. The percent loss in peak resolution due to the on-column detector is in fact calculated to be less than 0.02% for retained components with partition constants between 1 and 10 on columns with lengths longer than 1 meter. This is negligible but will be even less if the diameter of the column is less than 150 μm. An example of nicely resolved components is shown in FIG. 3. The mobile phase was 70% acetonitrite and 30% water. The column was 60 cm in length and 200 μm in inner diameter and composed of fused silica. It was packed with 5 μm particles having octadecylsiloxane bonded thereto. The flow rate was 5.4 μl/minute; the inlet pressure was 350 atmospheres. The volume of the flow cell was 0.09 μl. The clean separation of components a–f is indicated in Table I below.

| Label | Identity | Elution Time (min) |
|-------|----------|--------------------|
| a | benzene | 10 |
| b | toluene | 10.7 |
| c | naphthalene | 12 |
| d | flourene | 17.8 |
| e | phenathacene | 20.5 |
| f | pyrene | 29 |

Figure 5:
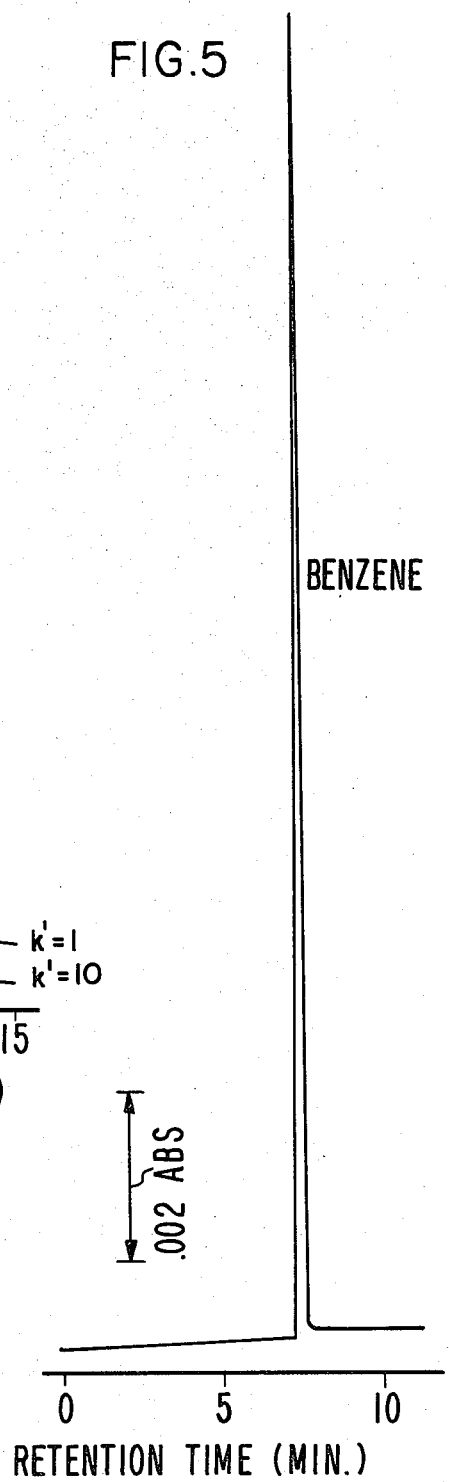
FIG. 5 is a chromatogram of benzene as detected by the apparatus of the present invention.

FIG. 5 shows the detection limit for a 6 μL on-column flow cell configured on the end of a 213 cm column. The detection limit was 0.24 nanograms of benzene which converts to a minimum detectable concentration of 1.5 nanograms/microliter. The flow rate was 1.06 μL/min. The peak height was of the order of one thousand times the noise.

What is claimed is:

1. A method for high resolution on-column detection in high resolution liquid chromatography, comprising:
providing a fused silica microcapillary column having an inner diameter less than 500 μm;
activating the interior of said column with a chromatographically active material;
applying a protective coating to the exterior of said column;
removing a segment of said protective coating to expose the underlying segment of said fused silica column;
providing an optical chromatographic detector;
positioning said exposed segment of said column in the optical path of said detector;
flowing a sample containing species to be identified through said column; and
detecting separated species as they flow through said exposed segment of said column.

2. A method for on-column detection in accordance with claim 1 wherein said step of activating the interior of said column is accomplished by the step of packing said column with a chromatographically active material and wherein said packing is removed within the volume of said exposed segment.

3. A method for on-column detection in accordance with claim 1 wherein said step of activating the interior of said column is accomplished by the step of coating the inner wall of said column with a chromatographically active material.

4. A method for on-column detection in accordance with claim 3 in combustion with the step of removing said chromatographically active material along said exposed segment.

5. A method for on-column detection in accordance with claim 1 wherein said step of providing a chromatographic detector is accomplished by the step of providing an ultraviolet absorbance detector.

6. Apparatus for on-column detection in high resolution liquid chromatography comprising:
a flexible fused silica column having an inner diameter less than 500 $\mu m$, said column being chromatographically activated and also having an external protective coating, said external coating having a segment exposed along the end of its length; and
an optical chromatographic detector configured to receive said column so that said exposed segment lies in the optical detection path of said detector.

7. Apparatus for on-column detection in accordance with claim 6 wherein said exposed segment is less than one centimeter in length.

8. Apparatus for on-column detection in accordance with claim 6 wherein said optical chromatographic detector is an ultraviolet detector.

9. Apparatus for on-column detection in accordance with claim 7 wherein said column is packed with a chromatographically active material.

10. Apparatus for on-column detection in accordance with claim 7 wherein the inner surface of said column is coated with a chromatographically active material.

* * * * *

UNITED STATES PATENT AND TRADEMARK OFFICE
CERTIFICATE OF CORRECTION

PATENT NO. : 4,375,163
DATED : March 1, 1983
INVENTOR(S) : FRANK JIANN-FU YANG

It is certified that error appears in the above-identified patent and that said Letters Patent is hereby corrected as shown below:

In column 7, line 2, replace "combustion" by --combination--.

Signed and Sealed this

Nineteenth Day of March, 1991

Attest:

HARRY F. MANBECK, JR.

*Attesting Officer*        *Commissioner of Patents and Trademarks*